United States Patent
Herron et al.

(10) Patent No.: US 9,851,468 B2
(45) Date of Patent: Dec. 26, 2017

(54) HYDROCARBON SATURATION FROM TOTAL ORGANIC CARBON LOGS DERIVED FROM INELASTIC AND CAPTURE NUCLEAR SPECTROSCOPY

(71) Applicant: Schlumberger Technology Corporation, Sugar Land, TX (US)

(72) Inventors: Michael M. Herron, Cambridge, MA (US); Susan Herron, Cambridge, MA (US); James A. Grau, Marshfield, MA (US); John P. Horkowitz, Sugar Land, TX (US); Paul R. Craddock, Scituate, MA (US); Robert Badry, Calgary (CA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 14/433,366

(22) PCT Filed: Oct. 4, 2013

(86) PCT No.: PCT/US2013/063358
§ 371 (c)(1),
(2) Date: Apr. 2, 2015

(87) PCT Pub. No.: WO2014/055810
PCT Pub. Date: Apr. 10, 2014

(65) Prior Publication Data
US 2015/0285944 A1 Oct. 8, 2015

Related U.S. Application Data

(60) Provisional application No. 61/709,850, filed on Oct. 4, 2012, provisional application No. 61/831,765, filed on Jun. 6, 2013.

(51) Int. Cl.
*G01V 11/00* (2006.01)
*G01N 33/24* (2006.01)
(Continued)

(52) U.S. Cl.
CPC .......... *G01V 11/00* (2013.01); *E21B 49/00* (2013.01); *G01N 33/246* (2013.01); *G01V 5/101* (2013.01)

(58) Field of Classification Search
CPC .................................................. G01V 11/00
See application file for complete search history.

(56) References Cited

U.S. PATENT DOCUMENTS 4,454,420 A    6/1984  Smith, Jr.
4,712,424 A *  12/1987 Herron .................. G01V 11/00
                                                 250/256
(Continued)

FOREIGN PATENT DOCUMENTS

RU    2090912 C1    9/1997
SU     483645 A1    9/1975
(Continued)

OTHER PUBLICATIONS

International Search Report for International Application No. PCT/US2013/063358 dated Feb. 13, 2014.
(Continued)

*Primary Examiner* — Edwin Gunberg
(74) *Attorney, Agent, or Firm* — Michael Dae

(57) ABSTRACT

The accurate determination of formation hydrocarbon or water saturation is a useful step in the petrophysical evaluation of petroleum reservoirs. This disclosure presents a new method for estimating hydrocarbon saturation directly from a porosity log and a total organic carbon (TOC) log. The method is enabled by the recent development of a geochemi-
(Continued)

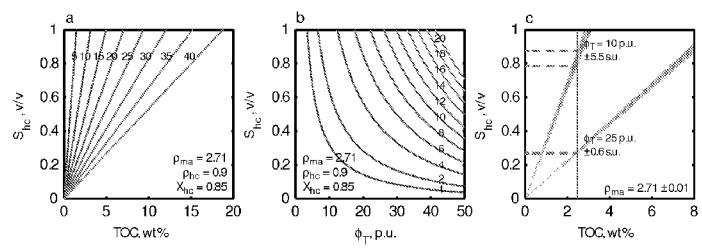

Sensitivity analyses exploring dependence of hydrocarbon saturation ($S_{hc}$) on variables TOC, porosity and matrix density. Calculations are shown for a limestone formation ($\rho_{ma}$ = 2.71 g/cm$^3$) with light oil ($\rho_{hc}$ = 0.90 g/cm$^3$, $X_{hc}$ = 0.85). (a) Saturation vs. TOC along lines of equal porosity. The near vertical lines at low porosity values demonstrate the sensitivity of $S_{hc}$ estimates to uncertainties in both TOC and porosity measurements in low porosity environments. For example, an uncertainty in TOC of ±0.5 wt% in a 10 p.u. reservoir is ±16 saturation units on $S_{hc}$, compared to ±10 saturation units in a 15 p.u. reservoir and ±5 saturation units in a 25 p.u. reservoir. (b) Saturation vs. porosity along lines of equal TOC. Saturation increases linearly with TOC, but inversely and asymptotically with porosity. The uncertainty in $S_{hc}$ estimations increases asymptotically with the uncertainty in porosity, as porosity decreases and approaches zero. (c) Saturation vs. TOC for a high (25 p.u.) and low porosity (10 p.u.) limestone. Gray bars indicate the uncertainty envelope about the $S_{hc}$ estimate arising from an uncertainty of ±0.01 g/cm$^3$ in the determination of matrix density. It can be observed again that uncertainties in $S_{hc}$ values are larger in low porosity environments (±5.5 s.u. compared to ±0.6 s.u.), even if the uncertainty on the matrix density input is constant. The consequence is that saturation interpretations are increasingly challenging in tight formations.

cal spectroscopy logging tool that combines inelastic and capture gamma ray measurements to provide a robust and accurate TOC log. The method differs from the prior approach of using carbon-to-oxygen ratios that is most often applied in cased hole evaluation. The main advantages of this method are that it does not use knowledge of formation water resistivity, it does not rely on a resistivity model, it does not use an extensive calibration database, and it is largely independent of clay or other lithology effects. Here, the principles of the method and the main challenges are described, and calculations that explore uncertainties in the saturation estimates arising from uncertainties in the log inputs are presented. The statistical uncertainty in the estimate of hydrocarbon saturation is as good as 10 saturation units (s.u.) in conventional reservoirs with porosities of 15 porosity units (p.u.) or greater. The method has been applied to the determination of hydrocarbon saturation in a variety of formations, including bitumen-filled dolomite, heavy oil sand, and shaly-sands with both open hole and cased hole wells. The method works equally well in formations drilled and logged with either oil- and water-based mud. The saturation estimates have been benchmarked against a combination of conventional and new logging approaches (e.g., resistivity, magnetic resonance and dielectric logs) and core measurements, with generally excellent agreement among independent determinations. Hydrocarbon saturations can be determined accurately using the method in a number of formation types where conventional methods and models for estimating fluid saturation commonly fail, such as freshwater and unknown water salinity in formations under enhanced oil recovery. The case studies included herein demonstrate that a TOC log derived from geochemical spectroscopy logs can be used to obtain reliable estimates of hydrocarbon saturation in a wide range of environmental conditions and formations.

12 Claims, 6 Drawing Sheets

(51) Int. Cl.
  *E21B 49/00* (2006.01)
  *G01V 5/10* (2006.01)

(56) References Cited

U.S. PATENT DOCUMENTS

| | | |
|---|---|---|
| 6,661,226 B1 | 12/2003 | Hou et al. |
| 7,366,615 B2 | 4/2008 | Herron et al. |
| 2015/0285944 A1 | 10/2015 | Herron et al. |

FOREIGN PATENT DOCUMENTS

| | | |
|---|---|---|
| SU | 1347067 A1 | 10/1987 |
| WO | 2014/055810 A1 | 4/2014 |

OTHER PUBLICATIONS

Jarvie "Shale Resource Systems for Oil and Gas: Part2-Shale-oil Resource Systems," The American Association of Petroleum Geologists, Aug. 2012 [online]. Retrieved from Internet: <URL: http://www.ourenergypolicy.org/wp-content/uploads/2012/08/CHAPTER1PART2.pdf>.
Radtke, et al. "A New Capture and Inelastic Spectroscopy Tool Takes Geochemical Logging to the Next Level," SPWLA 53rd Annual Logging Symposium, Cartagena, Colombia, Jun. 16-20, 2012, pp. 1-16.
Herron et al., "Total Organic Carbon and Formation Evaluation with Wireline Logs in the Green River Oil Shale," Oct. 30-Nov. 2, 2011, 19 pages, SPE 147184-PP, SPE Annual Technical Conference and Exhibition held in Denver, Colorado, USA.
Al-Harbi, A., Schmitt, D.P. and Ma, S.M. 2011. Toward Quantitative Remaining Oil Saturation (ROS): Determination Challenges and Techniques. Paper SPE 147651 presented at the SPE Annual Technical Conference and Exhibition, Denver, Colorado, Oct. 30-Nov. 2. (8 pages).
Charsky, A. and Herron, S. 2013. Accurate, Direct Total Organic Carbon (TOC) Log from a New Advanced Geochemical Spectroscopy Tool: Comparison with Conventional Approaches for TOC Estimation. AAPG 1547013. AAPG Annual Conference and Exhibition, Pittsburgh, Pennsylvania, May 20-22. (17 pages).
Curtis, C., Kopper, R., Decoster, E. et al. 2002. Heavy-oil Reservoirs. Oilfield Review 14 (3): 30-51.
Herron, M.M., Herron, S.L, Grau, J.A. et al. 2002. Real-time Petrophysical Analysis in siliciclastics from the Integration of Spectroscopy and Triple-combo Logging. Paper SPE 77631 presented at the SPE Annual Technical Conference and Exhibition, San Antonio, Texas, Sep. 29-Oct. 2. (7 pages).
Pickett, G.R. 1966. A Review of Current Techniques for Determination of Water Saturation from Logs. J. Pet Tech 18 (11):1425-1433.
Schultz, W.E. and Smith, H.D. 1974. Laboratory and Field Evaluation of a Carbon/Oxygen (C/O) Well Logging System. J. Pet Tech 26 (10): 1103-1110.
Timur, A. and Toksöz, M.N. 1985. Downhole geophysical logging. Annual Rev Earth Planet Sci 13: 315-344.
Woodhouse, R. and Kerr, S.A. 1988. The Evaluation of Oil Saturation Through Casing Using Carbon/Oxygen Logs. Paper SPE 17610 presented at the SPE International Meeting on Petroleum Engineering, Tianjin, China, Nov. 1-4. (12 pages).
International Search Report and written opinion for PCT Application PCT/US2013/063358 dated Feb. 13, 2014 (19 pages).
International Preliminary report on patentability for PCT Application PCT/US2013/063358 dated Apr. 7, 2015 (11 pages).
Office action issued in the related MX application MX/a/2015/004353 dated Apr. 13, 2016 (5 pages).
Office action issued in the related MX application MX/a/2015/004353 dated Sep. 14, 2016 (11 pages).

* cited by examiner

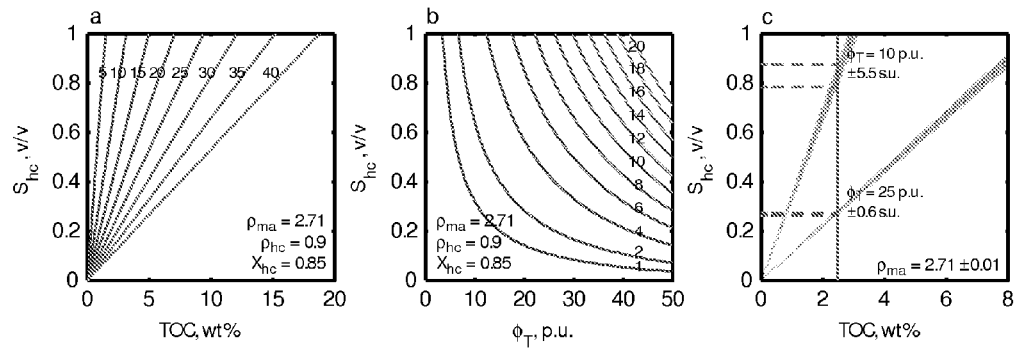

Fig. 1—Sensitivity analyses exploring dependence of hydrocarbon saturation ($S_{hc}$) on variables TOC, porosity and matrix density. Calculations are shown for a limestone formation ($\rho_{ma}$ = 2.71 g/cm³) with light oil ($\rho_{hc}$ = 0.90 g/cm³, $X_{hc}$ = 0.85). (a) Saturation vs. TOC along lines of equal porosity. The near vertical lines at low porosity values demonstrate the sensitivity of $S_{hc}$ estimates to uncertainties in both TOC and porosity measurements in low porosity environments. For example, an uncertainty in TOC of ±0.5 wt% in a 10 p.u. reservoir is ±16 saturation units on $S_{hc}$, compared to ±10 saturation units in a 15 p.u. reservoir and ±5 saturation units in a 25 p.u. reservoir. (b) Saturation vs. porosity along lines of equal TOC. Saturation increases linearly with TOC, but inversely and asymptotically with porosity. The uncertainty in $S_{hc}$ estimations increases asymptotically with the uncertainty in porosity, as porosity decreases and approaches zero. (c) Saturation vs. TOC for a high (25 p.u.) and low porosity (10 p.u.) limestone. Gray bars indicate the uncertainty envelope about the $S_{hc}$ estimate arising from an uncertainty of ±0.01 g/cm³ in the determination of matrix density. It can be observed again that uncertainties in $S_{hc}$ values are larger in low porosity environments (±5.5 s.u. compared to ±0.6 s.u.), even if the uncertainty on the matrix density input is constant. The consequence is that saturation interpretations are increasingly challenging in tight formations.

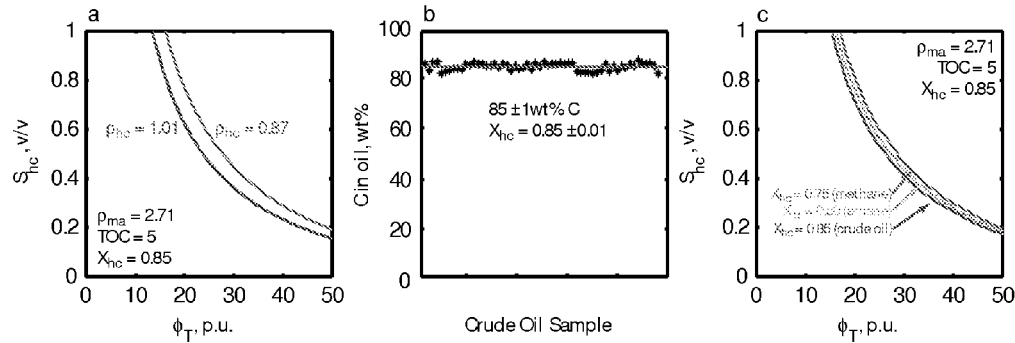

Fig. 2—Sensitivity analyses exploring dependence of hydrocarbon saturation ($S_{hc}$) on variables hydrocarbon density ($\rho_{hc}$) and carbon index ($X_{hc}$). Calculations are shown for a limestone formation ($\rho_{ma}$ = 2.71 g/cm³). (a) Saturation plotted vs. porosity shown for a hypothetical limestone formation containing 5 wt% total organic carbon, with density of light oil (green, $\rho_{hc}$ = 0.83 g/cm³) or extra heavy oil/bitumen (red, $\rho_{hc}$ = 1.03 g/cm³). The hydrocarbon density is assigned and has no statistical uncertainty; however, a correct assignment is helpful for the accurate computation of hydrocarbon saturation. (b) Carbon index—weight fraction of organic carbon in hydrocarbon—for petroleum crude oils as compiled by Speight (1999). The data indicate that the carbon index is near uniform among crude oils at 0.85 ±0.01; this value can be used in for all oil-bearing reservoirs. (c) Saturation vs. porosity for different values of $X_{hc}$. Given the limited range of $X_{hc}$ in petroleum crude oil, computed saturation is relatively insensitive to the assignment for $X_{hc}$. A rare exception would be for formations bearing light gases such methane ($CH_4$, $X_{hc}$ = 0.75) or ethane ($C_2H_6$, $X_{hc}$ = 0.80), or in coal bearing formations ($X_{hc}$ ~ 0.90).

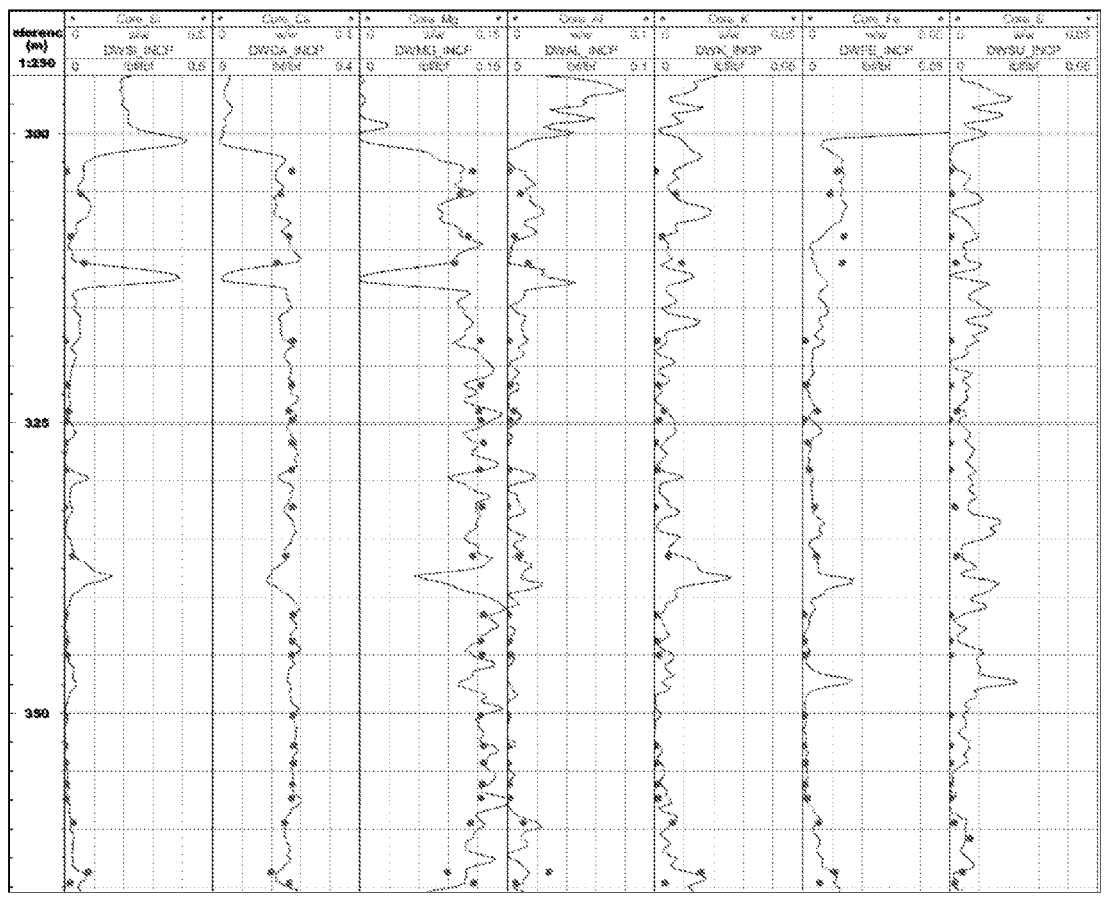

Fig. 3— Example 1: Element weight fraction on a dry-weight basis derived from combined inelastic and capture gamma spectroscopy logging. Core data are shown for comparison, showing that the agreement between log and core is generally very good. The systematically higher S content from log versus core is attributable to S in bitumen. Core chemical analyses are performed on clean core after oil removal by Dean Stark.

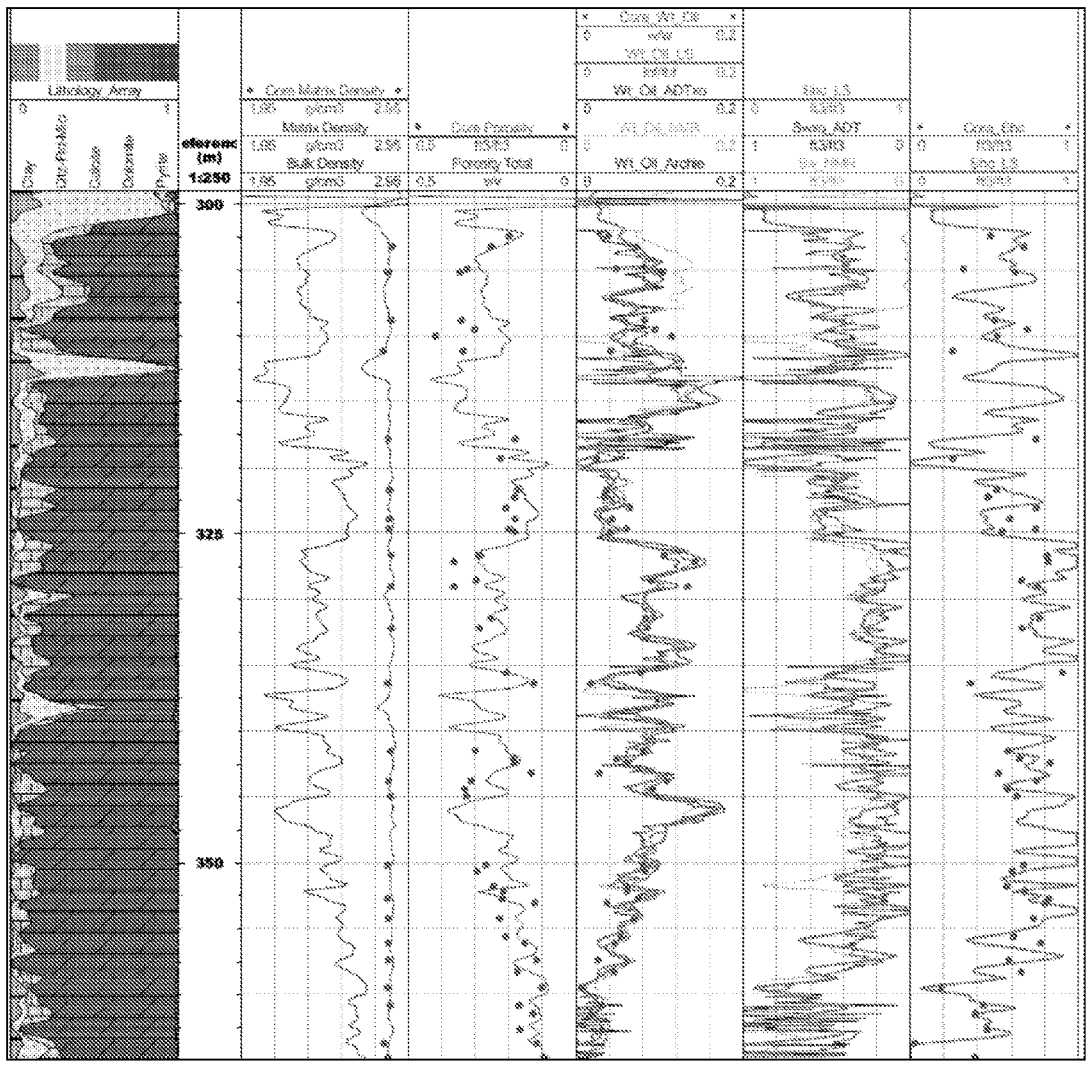

Fig. 4— Example 1: Petrophysical evaluation of bitumen-bearing dolomite. The interpretation shows the lithology (Track 1), log and core estimates of matrix density (Track 2) and porosity computed from bulk density and level-by-level matrix density (Track 3. Note in Track 4 the good agreement among the independent estimates of hydrocarbon concentrations, expressed as dry-weight fractions of oil, from log measurements (spectroscopy—green, resistivity—black, dielectric—blue, and magnetic resonance—orange) and from Dean Stark core analysis. Track 5 shows the favorable agreement among the spectroscopy-, magnetic resonance-, and dielectric-based determinations of fluid saturations in this formation. Track 6 compares the spectroscopy-derived hydrocarbon saturation against core oil saturations computed from weight fraction of oil recovered by Dean Stark, with favorable agreement between the new log method and the core benchmark.

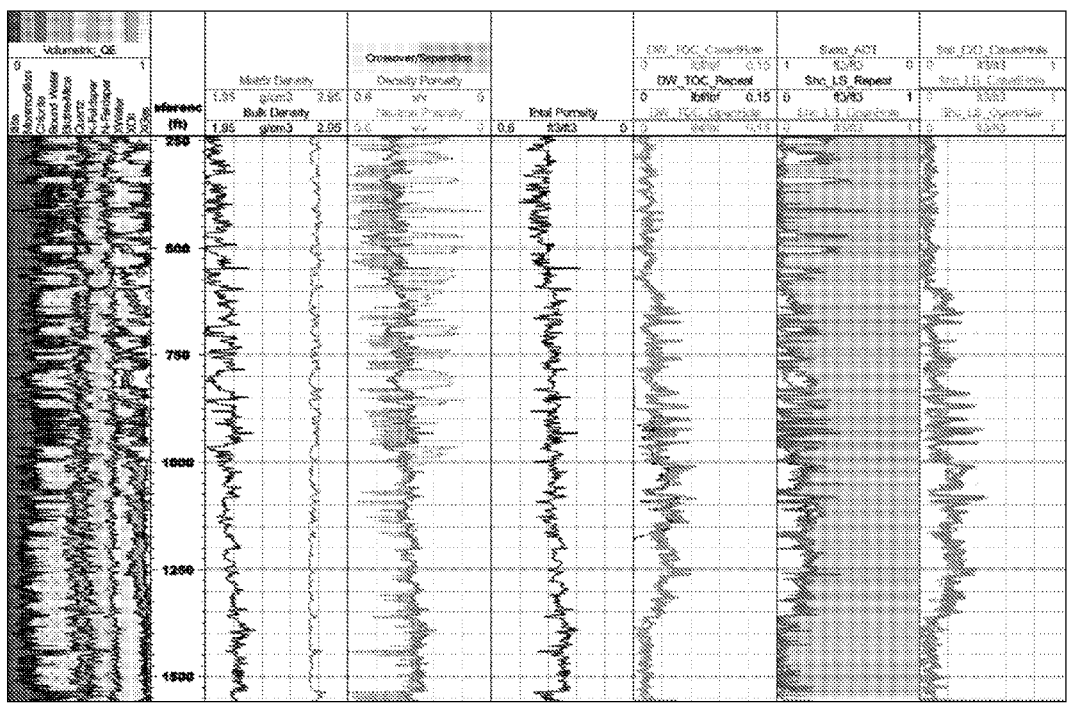

Fig. 5— Example 2: Petrophysical evaluation of heavy oil sandstone under enhanced recovery. In this example, hydrocarbon saturation is computed from TOC logs derived from nuclear spectroscopy logging in both open hole and cased hole. The density- and neutron-derived porosity logs (Track 3) show crossover in the interval above 1000 ft, which is currently under steam injection and is bearing gas phase. In the presence of gas, total porosity (Track 4) was computed from a weighted average of the density and neutron porosity logs). Track 5 compares the TOC log interpretations from both open hole (main pass—green, repeat pass—black; 875-1175 ft) and cased hole (main—gray), with excellent agreement between the different logs. Track 6 shows the hydrocarbon saturation log derived from TOC in open hole (green), compared against water saturation estimated from dielectric water-filled porosity (blue). The two logs show favorable agreement in the lower TOC bearing interval below 1000 ft, but diverge regularly in the overlying interval under steam injection, the difference being pore volume occupied by steam and/or air. The saturation log derived from geochemical spectroscopy and TOC should provide a more accurate prediction of residual oil saturation than logging methods based on deriving water saturation and inferring oil saturation. Track 7 compares the hydrocarbon saturation log derived from TOC in cased hole (gray) against oil saturation determined in cased hole from carbon/oxygen logging (red). Also shown for comparison is the hydrocarbon saturation log obtained previously in open hole (green). All logs compare favorably, demonstrating that accurate TOC and hydrocarbon saturation logs can be obtained by geochemical spectroscopy logging methods in cased hole as well as open hole.

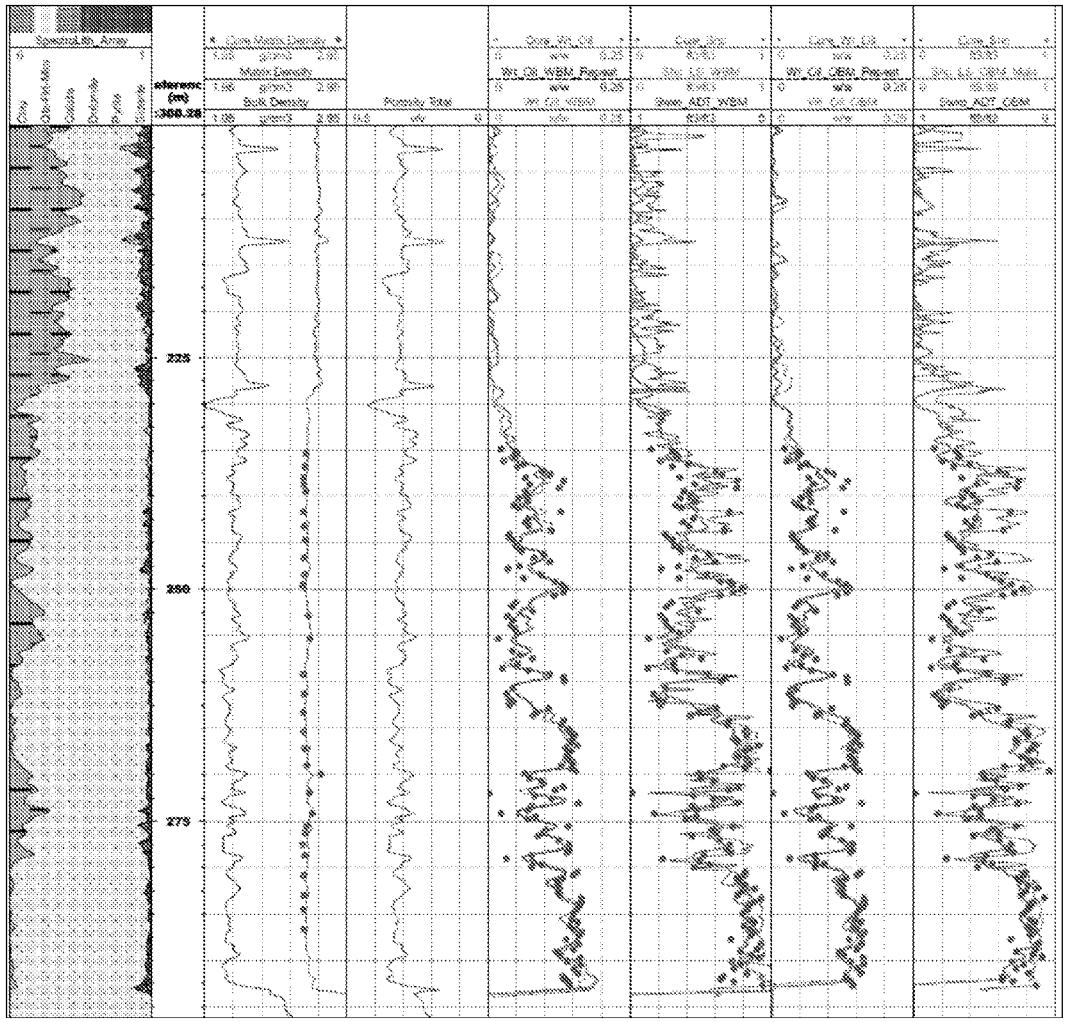

Fig. 6— Example 3: Petrophysical evaluation in oil sands. Logging was carried out in the same well both in water-based (WBM) and oil-based mud (OBM) using nuclear spectroscopy and dielectric sondes. Track 4 shows the WBM estimates of the dry-weight fraction of oil computed from log TOC/0.85 (main pass—green, repeat pass—black) compared against mass fractions of oil measured by core analyses, with good agreement. The TOC log was used to derive hydrocarbon saturation in WBM, shown and compared in Track 5 against water saturation obtained from dielectric water-filled porosity and against core oil saturations obtained from core mass fractions of oil. Again, the agreement between the three saturation estimates is favorable. Similarly, Track 5 shows dry-weight fractions of oil derived from TOC logs in OBM (main pass—green, repeat pass—black) compared against the mass fractions of measured oil. The final track shows hydrocarbon saturation derived from log TOC and water saturation obtained from dielectric log water-filled porosity in OBM. Both are compared against oil saturation derived from core mass fractions or oil. The concordance between the log and core estimates in both WBM and OBM supports the utility of our new method to derive accurate hydrocarbon saturations from TOC logs in both borehole environments.

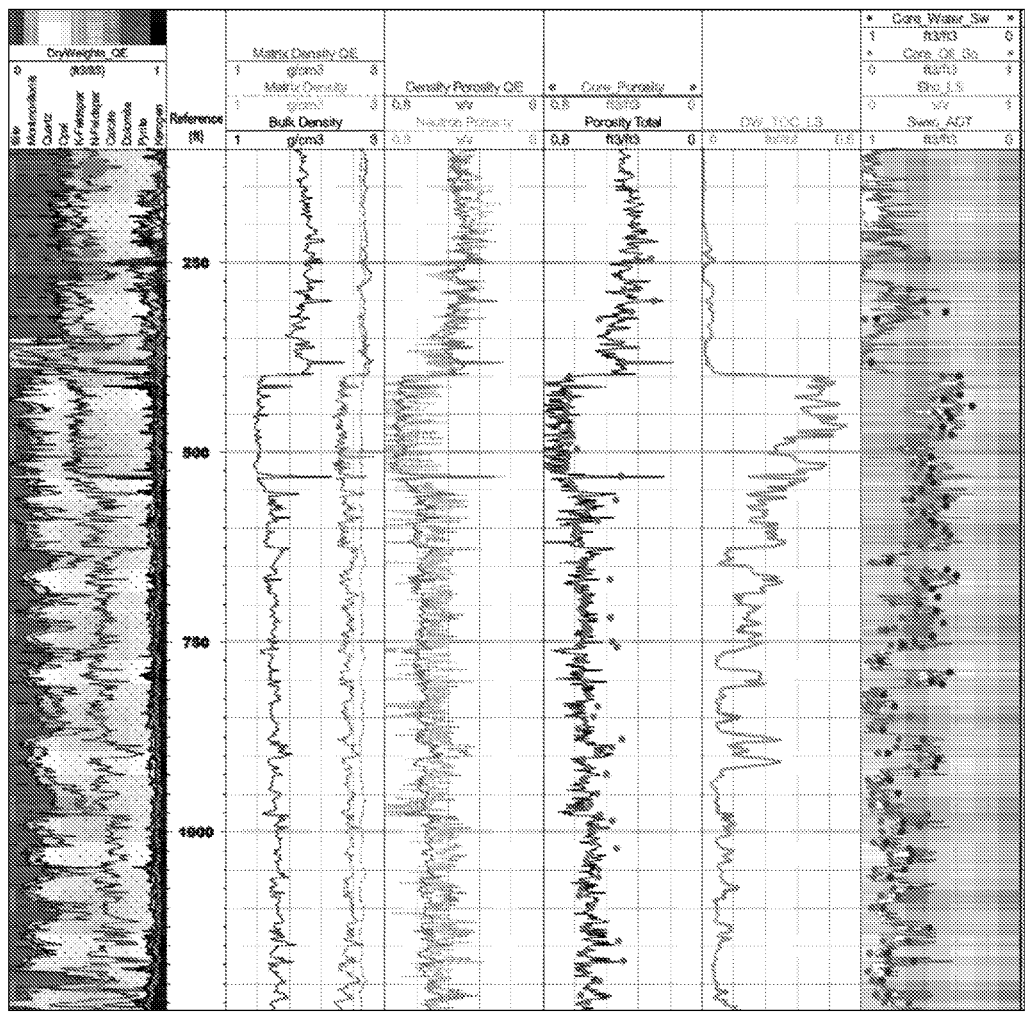

Fig. 7— Example 4: Petrophysical evaluation of a finely bedded and highly porous siliceous formation (Track 1). Connate water salinity is fresh and resistivity-based estimates of fluid saturations in this formation have proven difficult to obtain. Track 2 shows the apparent bulk density and two estimates of matrix density. The matrix density (solid blue) was derived from dry-weight mineral fractions obtained by solving a matrix inversion (QE). The porosities derived from a neutron log and a density log, using the matrix density computing from the matrix inversion, are shown in Track 3, and were combined to derive a weighted-average total porosity (Track 4) used in saturation evaluations. The computed total porosity matches well to core estimates of porosity. Track 5 shows the TOC log obtained from geochemical spectroscopy logs; TOC on a dry-weight basis is up to 40 wt% in the diatomite interval. Hydrocarbon saturation computed from TOC, matrix density and total porosity is shown in the final track. Also shown in this track is water saturation computed from dielectric water-filled porosity. The two log estimates visually compare favorably. Also shown are core estimates from retort analysis of oil and water saturations, which agree well with the respective log estimates of fluid saturations.

HYDROCARBON SATURATION FROM TOTAL ORGANIC CARBON LOGS DERIVED FROM INELASTIC AND CAPTURE NUCLEAR SPECTROSCOPY

BACKGROUND

The accurate determination of formation fluid saturation (e.g., hydrocarbon or water saturation) is a useful step in the petrophysical evaluation of conventional reservoirs. Commonly, open-hole resistivity-based models together with porosity logs are used for water saturation estimations owing to their availability, robustness and deep depth of investigation. To be accurate, however, these models utilize knowledge of formation water salinity (i.e., formation water resistivity) and formation properties (e.g., tortuosity factor, cementation exponent, corrections for matrix conductivity), and these models may fail in environments with low or unknown salinity, or with abundant and varying clay content. A quantitative estimation of remaining hydrocarbon saturation in reservoirs under enhanced oil recovery, such as water or steam flood, is particularly challenging using resistivity-based models because of differences in salinity of formation and injection waters and the effect of imbibitions on the saturation exponent, yet is useful for assessing hydrocarbon sweep efficiency and predicting future hydrocarbon production (Al-Harbi et al., 2010). Incorrect log analyst assignments in resistivity-based models can lead to significantly erroneous determinations of fluid saturations.

Formation sigma and inelastic carbon/oxygen logging are two common techniques for water or hydrocarbon saturation determination in cased-hole environments. Formation sigma is sensitive primarily to chloride in water. Similar to resistivity-based logging, this approach utilizes knowledge of formation salinity in order to estimate water volumes and has poor sensitivity in reservoirs with fresh waters. It also uses knowledge of matrix sigma. Salinity-independent inelastic carbon/oxygen logging is often used for saturation evaluation behind casing in environments with low or unknown salinity. In this technique, gamma ray energy spectra are decomposed into net inelastic yields from C and O, and capture yields from matrix elements (e.g., Si, Ca, Fe). A lithology-dependent model is used to partition C and O yields into respective contributions from the rock matrix, pore fluids and borehole fluids and the model data are inverted to obtain an estimate of oil volume. Interpretation of carbon/oxygen logs is complex, using extensive calibration and knowledge of the formation lithology, because oxygen is ubiquitous in the rock matrix and in formation and borehole fluids, and carbon is commonly present both in organic and inorganic formation components. The log adjustment for rock matrix contributions and uncertainties of the derived formation fluid carbon/oxygen ratio increase significantly at low porosities, so this method is typically applied in formations with porosities greater than 15 p.u.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

This disclosure presents a new method for estimating hydrocarbon saturation (Shc) from a total organic carbon (TOC) log derived from inelastic and capture gamma ray spectroscopy and porosity logs. The main advantages of this method compared to established log measurements are that it does not use knowledge of formation water resistivity or rely on a resistivity-based model, it does not use an extensive calibration database, and it is largely independent of clay or other lithology effects in many conventional formations. This disclosure first introduces the principles of the method and derivation of the algorithm used to compute Shc. Thereafter, calculations are presented which examine the sensitivity of Shc estimations to the log inputs and the uncertainties that arise in Shc estimates from uncertainties in those inputs. Following that, the application of the method to obtain accurate Shc log estimates from nuclear spectroscopy logs by way of several field studies in a range of geologic environments is demonstrated. The Shc estimates are benchmarked against a combination of conventional and new logging methods and core measurements that were used independently to derive formation saturation, with generally excellent agreement among independent estimates.

BRIEF DESCRIPTION OF THE DRAWINGS

FIG. 1a displays hydrocarbon saturation as a function of TOC for given levels of constant porosity.

FIG. 1b shows hydrocarbon saturation as a function of porosity for different concentrations of TOC.

FIG. 1c shows hydrocarbon saturation vs. porosity along lines of equal TOC.

FIG. 2a shows Shc computed using representative densities for light crude oil (0.83 g/cm$^3$) and natural bitumen (1.01 g/cm$^3$).

FIG. 2b illustrates the carbon index of crude oils ranging from light oil to heavy oil (Speight, 1999), with an average carbon index of 0.85±0.01 (i.e., 85% carbon by mass).

FIG. 2c shows hydrocarbon saturation vs. porosity for different values of the carbon index.

FIG. 3 compares dry-weight element logs derived from inelastic and capture spectroscopy against core data determined by X-ray fluorescence analyses also plotted on dry-weight basis.

FIG. 4 shows logs of bitumen-bearing dolomite determined using the method of this disclosure.

FIG. 5 shows logs of heavy oil sandstone determined using the method of this disclosure.

FIG. 6 shows logs of oil sands determined using the method of this disclosure.

FIG. 7 shows logs of a finely bedded and highly porous siliceous formation using the method of this disclosure.

DETAILED DESCRIPTION

One or more embodiments of the present disclosure will be described below. These described embodiments are only examples of the presently disclosed techniques. Additionally, in an effort to provide a concise description, all features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill in the art having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

The estimation of hydrocarbon saturation using nuclear spectroscopy logs is made possible by the development of a new spectroscopy tool that acquires gamma ray spectra from both fast neutron inelastic and thermal neutron capture reactions to quantify total carbon and key formation elements including Si, Ca, Mg, Fe, Ti and S. The geochemical spectroscopy logs enable a level-by-level determination of dry-weight element concentrations, matrix density, mineral volume and weight fractions, and TOC. Hydrocarbon saturation is computed directly from these parameters in combination with a porosity log.

The petrophysical interpretation includes first computing element dry-weight fractions including total carbon (e.g., $W_{Si}$, $W_{Ca}$, $W_{Mg}$, $W_{Fe}$, $W_s$, $W_K$, $W_C$) from the inelastic and capture spectral yields. These dry-weight fractions are used to estimate the fractional abundance by mass and/or volume of matrix minerals including, but not limited to, clay, quartz, calcite, dolomite, siderite, anhydrite, and pyrite. Computation of TOC is straightforward. Total inorganic carbon, the fraction of the measured total carbon contributed by the rock matrix, is calculated from the weight fractions of all carbon-bearing inorganic minerals, predominantly carbonates, in the formation (e.g., Eq. 1).

$$\text{Total Inorganic Carbon} = (0.12 W_{calcite} + 0.13 W_{dolomite} + 0.104 W_{siderite} + \ldots) \quad (1)$$

where the coefficients represent the weight fraction of carbon in the respective carbonate mineral. These coefficients are well known for carbonate minerals. Any and all carbon-bearing inorganic formation components can be including in this computation. TOC is then computed as the difference between the total carbon and total inorganic carbon:

$$\text{Total Organic Carbon (TOC)} = \text{Total Carbon} - \text{Total Inorganic Carbon} \quad (2)$$

TOC is reported as the weight fraction of organic carbon per unit mass of matrix components in the formation (i.e., dry-weight basis). It has been demonstrated that this estimate of TOC from geochemical spectroscopy logs agrees favorably with conventional TOC measurements from core also reported on a dry-weight basis. Note that this definition of TOC is different than that used in analytical communities, where TOC is typically reported per unit mass of formation. For non-source rocks, including conventional oil-bearing carbonates and sandstones, TOC measured in situ by a spectroscopy log can reasonably be assumed to exist as oil (or gas) in formation pore space and so can be used to compute the formation hydrocarbon saturation.

Saturation is defined as the fraction of total pore volume (i.e., porosity) that is occupied by the fluid of interest. In the case of hydrocarbon, this is, $$S_{hc} = \Phi_{hc} / \Phi_T, \quad (3)$$

where $\Phi_{hc}$ is the hydrocarbon-filled porosity and $\Phi_T$ is the total porosity, and where both porosities are defined as fractions relative to that of a unit volume of the formation. In order to derive the hydrocarbon-filled porosity, it is useful to compute hydrocarbon volumes from the TOC log. Noting that TOC is defined as the weight fraction of organic carbon relative to the mass of dry-weight matrix components ($M_{ma}$), we have, $$TOC = \frac{M_{TOC}}{M_{ma}}. \quad (4)$$

The mass of TOC is related to the mass of total hydrocarbon by the coefficient $X_{hc}$, which corresponds to the weight fraction of carbon in hydrocarbon, hereafter referred to as the carbon index, $$M_{TOC} = X_{hc} \cdot M_{hc}, \quad (5)$$

Assuming a unit volume, TOC can be expressed in terms of the component volumes and densities, $$TOC = \frac{X_{hc} \cdot \rho_{hc} \cdot \phi_{hc}}{\rho_{ma} \cdot \phi_{ma}} = \frac{X_{hc} \cdot \rho_{hc} \cdot \phi_{hc}}{\rho_{ma} \cdot (1 - \phi_T)} \quad (6)$$

By rearranging, this relationship can be expressed as a hydrocarbon volume, $$\phi_{hc} = \frac{TOC \cdot \rho_{ma} \cdot (1 - \phi_T)}{X_{hc} \cdot \rho_{hc}}, \quad (7)$$

and as a saturation, $$S_{hc} = \frac{\phi_{hc}}{\phi_T} = \frac{TOC \cdot \rho_{ma} \cdot (1 - \phi_T)}{X_{hc} \cdot \rho_{hc} \cdot \phi_T}. \quad (8)$$

It is worth noting that this equation does not include any environmental parameters or use a local calibration. Current carbon/oxygen log interpretations are typically computed with the carbon density value (CDV) of the hydrocarbon as a known input. CDV is equal to $X_{hc} \cdot \rho_{hc}$, so an alternative form of the saturation equation using CDV is:

$$S_{hc} = \frac{\phi_{hc}}{\phi_T} = \frac{TOC \cdot \rho_{ma} \cdot (1 - \phi_T)}{CDV \cdot \phi_T}. \quad (9)$$

To compute $S_{hc}$ from TOC also uses knowledge of the formation matrix density and porosity. Matrix density, $\rho_{ma}$, is computed on a level-by-level basis from, for example, elemental dry-weight fractions or mineral weight fractions obtained from geochemical spectroscopy logs. Porosity, $\Phi_T$, can be determined from several known log measurements, including but not limited to density, neutron, and sonic, or a combination thereof. In most cases, a gamma bulk density log is available, and a level-by-level matrix-corrected porosity is calculated from the bulk density and matrix density logs as follows:

$$\phi_T = \frac{\rho_{ma} - \rho_{bulk}}{\rho_{ma} - \rho_{fluid}}. \quad (10)$$

In this equation, $\rho_{fluid}$ is the bulk fluid density—the weighted average density of water and hydrocarbon in pore space—and is commonly fixed to 1.0 g/cm³ in oil-bearing reservoirs. In the presence of gas, porosity can be obtained from a weighted average of the matrix-adjusted neutron and density porosities (e.g., Herron et al., 2002).

Sensitivity and Error Analysis

Calculations have been carried out to examine the sensitivity of saturation estimations to uncertainties or systematic errors in the governing log parameters, TOC, $_{ma}$, $\Phi_T$, $_{hc}$, and $X_{hc}$, for a range of values that approximate conventional reservoir environments. FIGS. 1 and 2 show the results of these calculations. The calculations indicate that the precision of saturation determinations under logging conditions optimized for TOC measurements is as good as 10 s.u. in formations with porosities of 15 p.u. or greater.

Total Organic Carbon

The statistical uncertainty in TOC logs from combined inelastic and capture spectroscopy is dictated by local environmental and logging conditions. Logging parameters are optimized to reduce uncertainties in the computed elemental dry-weight fractions, such that precisions on TOC are typically 0.5 to 1.0 wt %. Comparisons of TOC from core and log measurements from numerous conventional and unconventional reservoirs have demonstrated that the spectroscopy-derived TOC estimate is accurate within this range. FIG. 1a displays hydrocarbon saturation as a function of TOC for given levels of constant porosity. Other parameters are held constant. The figure shows that hydrocarbon saturation increases linearly with TOC. However, the dependence between saturation and TOC varies significantly with porosity, becoming increasingly sensitive at lower porosities. Consequently, uncertainties in the estimate of $S_{hc}$ arising from uncertainties in the determination of TOC differ with the porosity of the formation. An uncertainty of ±0.5 wt % absolute in TOC forces an uncertainty of 4.2, 7.1, and 16 s.u. on the $S_{hc}$ estimate in a formation with a porosity of 30, 20, and 10 p.u., respectively. From a practical standpoint, improved precision of the TOC determination is useful at lower porosities to maintain acceptable uncertainties in $S_{hc}$ estimations.

Matrix Density and Porosity

The matrix density derived from geochemical spectroscopy logs has a statistical uncertainty of ±0.01 g/cm³ or better, under logging conditions used for TOC and hydrocarbon saturation interpretations. This uncertainty, relative to the matrix density of conventional reservoirs (e.g., quartz=2.65 g/cm³, limestone=2.71 g/cm³, dolomite=2.85 g/cm³) is much less than 0.5 to 1% relative. The resulting uncertainty in $S_{hc}$ determinations owing only to uncertainties in $_{ma}$ is less than 1 s.u. for reasonable values of formation porosity, even at less than 10 p.u.

Where the level-by-level matrix density is used with bulk density to obtain a total porosity log, uncertainties in the determination of matrix density map onto the computed density porosity. An uncertainty in $_{ma}$ of ±0.01 g/cm³ is equal to an uncertainty in $\Phi_T$ of approximately ±0.5 p.u. FIG. 1b shows hydrocarbon saturation as a function of porosity for different concentrations of TOC. The relationship between $S_{hc}$ and $\Phi_T$ is inverse and non-linear; therefore, uncertainties in hydrocarbon saturation estimates become increasingly large as porosity is reduced, even if the absolute uncertainty in the porosity determination is constant. This is demonstrated in FIG. 1c by way of example. Hydrocarbon saturation is shown computed as a function of TOC for a limestone formation with two porosity regimes. The first is a limestone with matrix and bulk densities of 2.71±0.01 and 2.28 g/cm³, respectively, corresponding to a porosity of 25±0.5 p.u. The second is a limestone with matrix and bulk densities of 2.71±0.01 and 2.54 g/cm³, respectively, corresponding to a porosity of 10±0.5 p.u. The associated uncertainty in the saturation estimate arising from a ±0.5 p.u. uncertainty in a 25 p.u. rock is less than 1 s.u., but is up to 6 s.u. in a 10 p.u. rock.

Hydrocarbon Density and Carbon Index

Neither the density, $_{hc}$, nor carbon index, $X_{hc}$, of the hydrocarbon phase can be measured directly by spectroscopy log methods and so may be assigned in the computation of hydrocarbon saturation from TOC logs. Light crude oils have densities less than 870 kg/m³ [gravity greater than 31.1° API], whereas extra heavy oils and natural bitumen have densities greater than 1000 kg/m³ [gravity less than 10° API]. The density of crude oil differs by over 15% relative. FIG. 2a shows $S_{hc}$ computed using representative densities for light crude oil (≤0.87 g/cm³) and natural bitumen 1.00 g/cm³). In a formation with a porosity of 20 p.u. and a TOC content of 5 wt %, the $S_{hc}$ estimates differ by 15 saturation units (77 versus 62 s.u., respectively). The absolute difference decreases with decreasing TOC. The absolute difference decreases with increasing porosity, but conversely is larger at smaller porosities.

The carbon index (weight fraction of carbon in hydrocarbon, $X_{hc}$) of petroleum oil is remarkably uniform around a value of 0.85 (FIG. 2b), despite the wide range of organic components contained therein, including saturates, aromatics, resins and asphaltenes. Reservoirs that are exceptions and use a different value of $X_{hc}$ are those that host gas (e.g., methane, $X_{hc}$=0.75; ethane, $X_{hc}$=0.80) or coal ($X_{hc}$ up to 0.9).

Error Propagation

The 'most likely' error in the determination of hydrocarbon saturation can be estimated from propagation of statistical uncertainties associated with the determination of the governing parameters. The general formula is given by, $$\sigma^2_{S_{hc}} = \sum_{i=1} \left[ \left| \frac{\partial S_{hc}}{\partial x_i} \right| \cdot \sigma_{x,i} \right]^2, \tag{13}$$

where $\partial S_{hc}/\partial x_i$ is the sensitivity of computed $S_{hc}$ to each parameter $x_i$ (i.e., TOC, $_{ma}$, $_T$, $_{hc}$, $X_{hc}$) and $_x$ is the statistical uncertainty in the determination of $x_i$. The statistical uncertainties in the parameters are here taken to be uncorrelated. The sensitivities are approximations based on values of $x_i$ that are appropriate for oil-bearing formations. Table 1 summarizes the expected uncertainty in estimates of hydrocarbon saturation as a function of reservoir porosity. The calculations demonstrate that uncertainties increase significantly at porosities less than 10 p.u., so that—as is the case for all saturation logging methods—saturation determination becomes increasingly challenging in tight rocks.

TABLE 1

Summary of most likely uncertainties in saturation estimates

| Porosity (p.u.) | Uncertainty (s.u.) |
|---|---|
| 30 | 6 |
| 20 | 10 |
| 15 | 12 |
| 10 | 25 |

Applications of Geochemical Spectroscopy Logs for Saturation Determination

The following section presents several case studies demonstrating the use of TOC logs derived from capture and inelastic spectroscopy logs to obtain accurate saturation logs. The method has been applied to a variety of reservoirs with different lithologies, a range of porosities and different hydrocarbon types and concentrations. The TOC log, in combination with a matrix density log and a porosity log, is used to estimate hydrocarbon saturation. Total organic carbon, matrix density and density porosity are computed level-by-level directly from geochemical spectroscopy and density logs. Hydrocarbon density and carbon index are assigned on a per-formation basis dependent upon the local environment. The derived $S_{hc}$ saturation logs are benchmarked against independent estimates of pore fluid volumes and fluid saturations obtained from logs including resistivity, dielectric and magnetic resonance, and from core samples. Core data is assumed to be ground truth; however, it is important to recognize that core data have inherent uncertainties from fluid extraction processes and porosity measurements, and that core and logs commonly investigate different volumes of the formation.

Example 1

The first example is of a bitumen-bearing vuggy dolomite. Deriving accurate elemental weight fractions is the first step to obtaining the accurate lithology, TOC and matrix density logs used for saturation estimations. FIG. 3 compares dry-weight element logs derived from inelastic and capture spectroscopy against core data determined by X-ray fluorescence analyses also plotted on dry-weight basis. The absolute difference between dry-weight element concentrations from log and core is on average less than 2 wt % for the abundant matrix elements in this formation (Ca, Mg, and Si) and significantly less than 1 wt % for other matrix elements (Fe and K), supporting the accuracy of the geochemical logging measurements. The exception is the element sulfur, for which log data are systematically higher compared to core by 1 to 2 wt %. This difference reflects S in bitumen, which was removed from core samples by cleaning prior to elemental analysis. It is possible from the dry-weight element logs to determine the weight fraction of sulfur in hydrocarbon. In situ log sulfur measurement includes sulfur both in inorganic formation components (for example pyrite and anhydrite, among others) and in hydrocarbon (kerogen, bitumen, oil, etc). The inorganic associated sulfur can be determined from log mineral abundances—for example, in the case of pyrite, this is determined as $S_{pyrite}=0.535*W_{pyrite}$. The excess sulfur in hydrocarbon components is the difference between the total log sulfur and inorganic sulfur associated with all inorganic formation components. The ratio of the mass abundance of excess sulfur to mass abundance of hydrocarbon is the weight fraction of sulfur in the organic.

The dry-weight element logs were used to derive the level-by-level log lithology and matrix density, shown in FIG. 4, Tracks 1 and 2. Track 2 also shows matrix density measured on core samples against log matrix density, with good agreement between the two estimates. The bulk density and variable matrix density log were used to compute a total porosity log (Eq. 10), shown in Track 3. Also shown in Track 3 for comparison is porosity determined from core. Track 4 compares the mass fraction of oil (bitumen) determined from independent log (spectroscopy-green, resistivity-black, magnetic resonance-orange, and dielectric-blue) and core measurements. The mass fraction of oil from geochemical spectroscopy logs is calculated from TOC logs using the relationship, $Wt_{oil}=Wt_{TOC}/X_{hc}$ (c.f., Eq. 5), where $X_{hc}$ is the carbon index of oil with a value of 0.85. Mass fractions of oil computed from resistivity, magnetic resonance and dielectric log are computed from estimations of water and oil volumes, assuming a density for bitumen in this reservoir of ~1.01 g/cm$^3$ (gravity of 7 to 9° API; Curtis et al., 2002).

Core estimates of the mass fraction of oil are derived directly from core measurements. In Track 5, hydrocarbon saturation, is shown computed from the TOC, total porosity, and level-by-level matrix density logs, using $_{hc}$=1.01 g/cm$^3$ and $X_{hc}$=0.85 (Eq. 8). Log estimates of water saturation (plotted on reverse axis; $S_w=1-S_{hc}$) derived from magnetic resonance and dielectric log measurements are also shown in Track 5 for comparison. These logs were chosen specifically because the formation conditions are favorable for water saturation determinations by magnetic resonance and dielectric techniques, and they are generally accepted as providing good answers. NMR log measurements in this formation should be primarily sensitive to the presence of water because the bitumen viscosity is very high and most of the bitumen signal relaxation time is too short to be identified. The water volume from NMR is computed by applying a cutoff to the T2 distribution knowing that the bitumen relaxation time is less than 3 ms. For dielectric logs, the primary output is water-filled porosity. Thus, water saturation calculation from both NMR and dielectric measurements is a straight forward ratio of the water-filled porosity over the total porosity. In addition, the logs may be reporting saturations in the virgin reservoir because the high viscosity of bitumen will preclude invasion of borehole fluids into the formation. The comparison highlights the favorable agreement among the logs and validates the use of TOC logs derived from geochemical spectroscopy logging to give an accurate estimate of formation hydrocarbon saturation; for example, the average difference between geochemical spectroscopy and dielectric estimates of fluid saturations is less than 5 s.u.

In the final track, hydrocarbon saturation derived from geochemical spectroscopy and TOC logs is compared against oil saturation computed from core measurements of the mass fraction of oil recovered. Core derived oil volumes were computed from weight fractions using a bitumen density of 1.01 g/cm$^3$ as above, and were used in combination with core derived porosities to estimate oil saturations. The visual agreement between log and core estimates of hydrocarbon saturations is favorable throughout the cored interval. In detail, log derived hydrocarbon saturations are on average higher than core estimates by 7 s.u., which is explained by incomplete recovery of bitumen from core—as indicated by volumes fractions of water and oil relative to total pore volume that sum to less than 100%.

Example 2

The second example is of a high porosity, bedded shaly-sand producing heavy oil under enhanced recovery techniques (FIG. 5). Owing to very fresh formation waters (salinity less than 5 kppm), and variable temperature and salinity from extensive steam injection, resistivity-based estimates of residual oil saturation (ROS) in this field commonly fail. The lack of accurate ROS log measurements from resistivity uses the use of alternative technologies less sensitive to water salinity to optimize future reserves depletion. This example demonstrates the use of geochemical spectroscopy logging to determine ROS, and it is applicable to both open and cased hole.

For this interpretation, a matrix inversion was used to solve for volumetric and weight fractions of minerals and of pore fluids owing to the complex mineralogy in this formation. The inversion uses a set of pre-defined constraints (e.g., mineral and fluid densities and compositions) to minimize the difference between the measured log data (e.g., dry-weight element fractions, bulk density, neutron porosity, etc) and the modeled log data. FIG. 5, Track 1 shows the resulting volumetric interpretation, based on open hole log analysis. Track 2 shows the measured bulk density log and the matrix density log from open hole analysis. The large divergence between the logs results from the significant porosity in this formation. The bulk density and matrix density logs were used to compute a density-derived porosity log (Eq. 10), shown in Track 3.

Also shown in Track 3 for comparison is the thermal neutron porosity log ran in open hole. The density-derived porosity and neutron porosity logs converge in the lower interval, but show crossover in the interval above x1000 ft. The crossover is likely in response to the presence of steam or air (a gaseous phase), because this field is under enhanced oil recovery (EOR) and the logged interval includes the vadose zone. The crossover results from the response of the density and neutron log measurements to the presence of steam or air, with the density log reading too high a porosity and the neutron log too low. In the presence of a gaseous phase, total porosity (Track 4) was computed as a weighted average of the matrix-adjusted density and neutron estimates. This porosity estimate agrees within 1 to 2 p.u. with porosity predicted from the matrix inversion used to derive mineralogy.

Track 5 shows the TOC logs derived from spectroscopy logs ran in both open hole (green) and cased hole (gray). A repeat log was ran in the open hole, and the repeat TOC log (black) is compared against the main TOC log with excellent agreement and consistency. Both open hole TOC logs agree favorably with the cased hole TOC log, demonstrating that it is possible to derive consistent TOC estimations from spectroscopy logs in both types of hole, despite the different environmental logging conditions and environmental corrections.

Tracks 6 and 7 show the hydrocarbon saturations derived from open hole and cased hole TOC log measurements, respectively. The open hole matrix density and total porosity logs (Tracks 2 and 4) were used for both the open hole and cased hole saturation computations. The gravity of oil in this field is between 10 and 14° API ($_{hc}$~0.98±0.01 g/cm³) and the carbon index was assigned a value of 0.85. The $S_{hc}$ log estimates from the open hole main and repeat spectroscopy and TOC logs show excellent agreement (Track 6). Open hole water saturation, $S_w$, derived from dielectric water-filled porosity is also shown for comparison against the spectroscopy derived estimates. The two independent log measurements practically overlay in the lower interval. The hydrocarbon saturation derived from TOC and the water saturation derived from dielectric diverge in the overlying interval where steam and/or air is present. By using a combination of two or more independent saturation measurements, it is possible to identify fluids and quantify fluid saturations in a multi-phase environment comprising liquid or solid hydrocarbon (for example, bitumen or oil), water, and gaseous phases (for example, air, steam, $CO_2$, or gas). In this example, saturation derived from spectroscopy and TOC, which is sensitive directly to volume of hydrocarbon, should provide a more accurate estimate of remaining oil in place, instead of alternative log techniques that are sensitive to the volume of water, and so infer that of hydrocarbon by difference.

Hydrocarbon saturation determined from the cased hole TOC log is shown and compared in Track 7 against that derived from the open hole TOC log, with good agreement between the estimates. This follows because spectroscopy derived TOC estimates in both open and cased hole were demonstrated previously to compare favorably (Track 5) and the same porosity was used for both determinations. A carbon/oxygen log was ran in cased hole and an oil saturation derived from carbon/oxygen (Track 7) was used as an independent estimate to validate the hydrocarbon saturation derived from cased hole TOC log. The porosity used to compute oil saturation from carbon/oxygen was computed from formation sigma, which was logged in cased hole at the same time as the carbon/oxygen logs. Hydrocarbon saturation derived from TOC in cased hole compares favorably against the independent measure of saturation from carbon/oxygen throughout the logged interval.

Example 3

The third example is a Canadian oil sands well that was cored over the zone of interest (FIG. 6). The density of heavy oil in this formation is 1.01 g/cm³. This well was logged in both water-based (WBM) and oil-based mud (OBM), and demonstrates the utility of nuclear spectroscopy logs to derive accurate TOC and hydrocarbon saturations in both borehole environments.

The dry-weight mineral fractions and matrix density computed from geochemical spectroscopy logs in WBM are shown in Tracks 1 and 2, respectively. Matrix density on an organic-free basis from core measurements is shown also in Track 2. Track 3 shows total porosity computed using the bulk density log and the level-by-level matrix density log from spectroscopy run in WBM. This porosity log was used in the determination of fluid saturations. Track 4 shows for the WBM example, the mass fraction of oil on a dry-weight basis computed from TOC assuming a carbon index of 0.85 (main pass—green, repeat pass—black). The mass fraction of oil recovered from core by Dean Stark is shown on a dry-weight basis for direct comparison. The agreement between oil weight fraction estimates from log and core is highly favorable.

Track 5 shows the WBM comparison between hydrocarbon saturations obtained from log (green) and core (red) measurements, with good agreement. Hydrocarbon saturation estimates from spectroscopy logs were computed in the manner described previously, here using an oil density of 1.01 g/cm³. Core saturations were derived from weight fractions of recovered oil using the same density of oil to compute oil volumes, and in the absence of core measured porosities, the porosity log derived from density logs was used as the porosity input. The core determinations reveal some sharp variations in saturation over vertical scales less than 1 ft that are not captured by TOC log-derived saturation, which has a vertical resolution in this well of 1.5 to 2 ft. Track 5 also shows a water saturation log (blue) derived from dielectric water-filled porosity logged in WBM. The spectroscopy and dielectric log fluid saturations again compare favorably, noting that the dielectric log shows fine scale heterogeneity in the saturation log as a result of the higher vertical resolution of the logging technique. Through the cored interval between x235 and x290 m, the average difference between fluid saturations obtained on the two sets of logs is less than 3 s.u., well within the statistical uncertainty of the log determinations.

Tracks 6 and 7 show the saturation interpretation obtained from logs in OBM. Estimates of TOC from the main and repeat spectroscopy logs in OBM agree favorably with each other and with those from core measurements; this concordance indicates that it is possible to obtain accurate TOC logs in OBM by correcting for the carbon contribution from OBM to the measured inelastic carbon spectra during spectroscopy log analysis. The last track compares hydrocarbon saturation computed from the main TOC log in OBM against the hydrocarbon saturation estimated from core TOC data (shown previously in Track 5). The log and core estimates again show good overall agreement, noting that core data again reveal vertical heterogeneity in oil saturations in this well that may not be captured by log. The dielectric-based determination of water saturation from water-filled porosity measurements in OBM is shown for comparison to the TOC derived determination of hydrocarbon saturation. Again, the two independent log measures of fluid saturations show very good agreement.

Example 4

The fourth example is of a finely bedded and highly porous diatomite (FIG. 7). Connate water salinity is fresh (5 kppm) and resistivity-based estimates of fluid saturations in this formation have proven difficult to obtain. The formation has a variable and complex lithology, which also complicates interpretations to obtain accurate fluid saturations. Given the complex lithology, a matrix inversion was used here to solve for volumetric and weight fractions of minerals, using the dry-weight element logs obtained from spectroscopy logs. The lithology interpretation, on a dry-weight basis, is shown in Track 1 and highlights the diatomite below x400 ft. Track 2 shows the apparent bulk density curve (black) compared to two estimates of matrix density. The standard means of computing matrix density from dry-weight element logs is shown by the dashed blue curve. This estimate of matrix density is likely biased high in the diatomite because the calibration to dry-weight silicon assumes a density for quartz-feldspar (2.57 to 2.65 g/cm$^3$), and does not account for silicon in opal with a density between 2.0 and 2.25 g/cm$^3$. The solid blue curve is the matrix density computed using the weight fractions of minerals derived from the matrix inversion, accounting for the presence of opal (density for opal equal to 2.25 g/cm$^3$). This matrix density estimated from the inversion was used to derive porosity and fluid saturation.

Track 3 shows the porosity computed from the bulk and level-by-level matrix density log derived from the matrix inversion. This is compared against a neutron porosity log. The neutron porosity log suffers at high porosity and here lacks sensitivity to small changes in porosity because of the effect of the high hydrogen content of pore fluids on the neutron log response. The matrix inversion was used to derive a total porosity, shown in Track 4, from matrix and neutron density logs. The total porosity log closely follows that of density porosity because of the low weighting applied to the statistical neutron log. Track 4 compares the estimate of total porosity against porosity determinations from core. The match is highly favorable, with the only systematic difference in the interval between x400 and x550 ft at the top of the diatomite. This difference of 3 to 5 p.u. likely reflects the assignment for the density of opal—a lower density for opal of 2.0 g/cm$^3$ would lower the log porosity by this amount.

Track 5 shows log TOC derived from geochemical spectroscopy logs, with TOC on a dry-weight basis is up to 40 wt % in the diatomite. Track 6 shows the saturation interpretations. Shown in green is the hydrocarbon saturation computed from TOC and spectroscopy logs, and from the total porosity log derived from matrix inversion (Track 4). The gravity of oil in this formation used to compute saturation is 17 to 19° API (i.e., 0.93 g/cm$^3$). Track 6 shows oil saturation determined from retort on core samples (red) for comparison against the TOC-based hydrocarbon saturation estimates. The agreement between the log and core saturation estimates is highly favorable throughout the entire interval.

Also shown in Track 6 is water saturation calculated from dielectric water-filled porosity. The same total porosity log used in the determination of oil saturation from TOC was used for the dielectric based water saturation. The agreement between log estimates is favorable, with the logs visually exhibiting the same trends. There is, however, a systematic difference between the two log estimates of approximately 5 to 10 s.u. Track 6 further shows water saturation determined from retort of core samples (blue) for comparison against the dielectric-based saturation. The agreement between the core and dielectric based water saturations is favorable. The agreement of both the TOC and dielectric-based log saturations to core estimates of oil and water saturation suggests that the difference of 5 to 10 s.u. between the two log estimates is real. This difference represents pore space occupied by a gaseous phase (such as steam or air) as the formation is under enhanced recovery.

As described above, the application of this method has been demonstrated in a variety of conventional oil reservoirs, including carbonates, sandstones and shaly sands, and reservoirs under varying stages of enhanced oil recovery. The case studies demonstrate the use of a TOC log derived from geochemical spectroscopy logs to obtain reliable estimates of hydrocarbon saturation, at the same time as lithology, across a wide range of formations and environmental conditions. Calculations indicate that hydrocarbon saturation uncertainties are as good as 10 saturation units in conventional reservoirs with porosities higher than 15 porosity units.

It should be readily understood that the various properties of subsurface formations from which the hydrocarbon saturation is determined can be determined from measurements of properties taken using natural gamma ray measurement tools, nuclear spectroscopy tools, induction and resistivity tools, and nuclear magnetic resistance imaging tools, as well as any other suitable tools, such as a sampling tool. The calculations can be performed by a computer system, either in real time as the various properties are measured, or from stored logs of the properties. The computer system may be directly or indirectly coupled to any tools used to measure the properties.

While the disclosure has been described with respect to a limited number of embodiments, those skilled in the art, having benefit of this disclosure, will appreciate that other embodiments can be envisioned that do not depart from the scope of the disclosure as disclosed herein.

Glossary of Terms

EOR=Enhanced oil recovery
$\phi_{hc}$ Hydrocarbon-filled porosity
$\phi_T$=Total porosity $M_x$=Mass of component x (e.g., TOC, matrix, formation)
$\rho_{hc}$=Hydrocarbon density
$\rho_{ma}$=Matrix density
p.u.=Porosity units
ROS=Residual oil saturation
$S_{hc}$=Hydrocarbon saturation
$S_w$=Water saturation
s.u.=Saturation units
TOC=Total organic carbon, expressed as dry-weight fraction
$W_i$=Weight fraction of element or mineral i
$X_{hc}$=Carbon index (i.e., carbon weight fraction in hydrocarbon)

The invention claimed is:

1. A method for determining properties of a subsurface formation comprising:
   emitting neutrons into a subsurface formation using a neutron source of a spectroscopy tool;
   detecting, via a gamma-ray detector of the spectroscopy tool, gamma rays induced by inelastic scattering of the neutrons emitted into the subsurface formation and gamma rays induced by thermal capture reactions of neutrons emitted into the subsurface formation;
   determining, via a processor of the spectroscopy tool, a total carbon measurement of the subsurface formation based on the detected gamma rays, a total inorganic carbon measurement based on a inorganic formation component of the subsurface formation, and a total organic carbon measurement based on the difference between the total carbon measurement and the total inorganic carbon measurement;
   determining, via the processor, a hydrocarbon-filled porosity of the subsurface formation based on the total organic carbon measurement;
   determining, via the processor, a total porosity of the subsurface formation; and
   computing, via the processor, a hydrocarbon saturation of the subsurface formation based upon a ratio of the hydrocarbon-filled porosity to the total porosity.

2. The method of claim 1, wherein the hydrocarbon-filled porosity is determined based upon a total organic carbon measurement of the subsurface formation, a matrix density measurement of the subsurface formation, a porosity measurement of the subsurface formation, and a carbon density value of the formation.

3. The method of claim 2, wherein the hydrocarbon-filled porosity is determined as a ratio of a product of the total organic carbon measurement, the matrix density measurement, and a volume of a matrix of the subsurface formation, to the carbon density value of the formation.

4. The method of claim 1, further comprising identifying a gaseous phase of the subsurface formation by evaluating a difference between the hydrocarbon saturation, and an independent estimate of a water saturation of the subsurface formation.

5. The method of claim 1, further comprising quantifying a multi-phase saturation of the subsurface formation based upon the hydrocarbon saturation and an independent quantification of other fluid phases and fluid saturations of the subsurface formation.

6. The method of claim 5, wherein the multi-phase saturation includes at least one of oil, water, and a gaseous phase.

7. The method of claim 6, where the gaseous phase present in the subsurface formation is determined from at least one of nuclear radiation measurements, sonic measurements, or nuclear magnetic resonance measurements.

8. The method of claim 4, where water saturation is determined by performing at least one of a resistivity measurement, dielectric measurement, and nuclear magnetic resonance measurement.

9. A method for determining a sulfur content of hydrocarbons in a subsurface formation comprising:
   emitting neutrons into a subsurface formation using a neutron source of a spectroscopy tool;
   detecting, via a gamma-ray detector of the spectroscopy tool, gamma rays induced by inelastic scattering of the neutrons emitted into the subsurface formation and gamma rays induced by thermal capture reactions of neutrons emitted into the subsurface formation;
   determining, via a processor of the spectroscopy tool, a total sulfur content of the subsurface formation based on the detected gamma rays;
   determining, via the processor, an amount of sulfur associated with inorganic components of the subsurface formation;
   determining, via the processor, the sulfur content of hydrocarbons in the subsurface formation by comparing the total sulfur content to the amount of sulfur associated with inorganic components.

10. The method of claim 9, wherein the amount of sulfur associated with inorganic components of the subsurface formation is determined from an estimation of formation mineralogy.

11. The method of claim 10 wherein the estimation of formation mineralogy is based upon a core measurement or the elemental spectroscopy technique.

12. The method of claim 9, where the amount of sulfur associated with inorganic components is directly measured on core samples from which organic matter has been removed.

* * * * *